US007321315B2

(12) United States Patent
Brumm et al.

(10) Patent No.: US 7,321,315 B2
(45) Date of Patent: Jan. 22, 2008

(54) SYSTEM AND METHOD FOR IDENTIFYING DISPOSABLE ABSORBENT PRODUCTS

(75) Inventors: Russell J. Brumm, Menasha, WI (US); Jason Cohen, Appleton, WI (US); Daniel L. Ellingson, Appleton, WI (US); Alissa Ellingson, Appleton, WI (US); Brian C. Eppstein, Appleton, WI (US); Sheng-Hsin Hu, Appleton, WI (US); Jennifer Marvin, Greenville, WI (US); Walter Reade, Appleton, WI (US); Brendon F. Ribble, Menasha, WI (US); Eric F. Wagner, Sherwood, WI (US); Dan Westbrook, Sherwood, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 740 days.

(21) Appl. No.: 10/749,790

(22) Filed: Dec. 29, 2003

(65) Prior Publication Data
US 2005/0148978 A1 Jul. 7, 2005

(51) Int. Cl.
G08B 3/00 (2006.01)
G08B 5/00 (2006.01)
G08B 7/00 (2006.01)
(52) U.S. Cl. .............................. 340/691.1; 340/572.1; 340/573.1
(58) Field of Classification Search ............. 340/691.1, 340/572.1, 573.1, 573.5, 692, 384.1; 235/385; 705/22, 28
See application file for complete search history.

(56) References Cited

U.S. PATENT DOCUMENTS

| 5,030,807 | A | 7/1991 | Landt et al. |
| 5,392,032 | A | 2/1995 | Kline et al. |
| 5,594,228 | A | 1/1997 | Swartz et al. |
| 5,890,717 | A | 4/1999 | Roseware et al. |
| 6,084,528 | A | 7/2000 | Beach et al. |

(Continued)

FOREIGN PATENT DOCUMENTS

JP 2003-058759 2/2003

(Continued)

OTHER PUBLICATIONS

"International Search Report for Application No. PCT/US2004/025863, Date mailed Nov. 26, 2004".

(Continued)

*Primary Examiner*—John Tweel, Jr.
(74) *Attorney, Agent, or Firm*—Schwegman, Lundberg & Woessner, P.A.

(57) ABSTRACT

The present invention relates to a system that includes a plurality of disposable absorbent products where at least one of the disposable absorbent products includes a tag. The system further includes a reader that identifies the tags on the plurality of disposable absorbent products and plays media based on the identity of the tags. In another form, the system includes a reader that identifies the tags on the plurality of disposable absorbent products and provides information relating to one other product based on the identity of the tags. In still another form, the present invention relates to a method that includes marking a plurality of disposable absorbent products (e.g., diapers) with a tag, and providing a reader that plays media based on the identity of the tags.

38 Claims, 11 Drawing Sheets

U.S. PATENT DOCUMENTS

| | | | |
|---|---|---|---|
| 6,092,726 A * | 7/2000 | Toussant et al. | 235/385 |
| 6,352,478 B1 | 3/2002 | Gabai et al. | |
| 6,360,181 B1 * | 3/2002 | Gemmell et al. | 705/22 |
| 6,429,768 B1 | 8/2002 | Flick | |
| 6,491,566 B2 | 12/2002 | Peters et al. | |
| 6,707,376 B1 | 3/2004 | Patterson et al. | |
| 6,707,381 B1 | 3/2004 | Maloney | |
| 6,753,783 B2 * | 6/2004 | Friedman et al. | 340/573.1 |
| 6,975,230 B1 * | 12/2005 | Brilman | 340/573.1 |
| 6,982,640 B2 * | 1/2006 | Lindsay et al. | 340/572.1 |
| 7,183,929 B1 * | 2/2007 | Antebi et al. | 340/573.1 |
| 7,209,044 B2 * | 4/2007 | Reustle | 340/573.5 |

FOREIGN PATENT DOCUMENTS

| | | |
|---|---|---|
| WO | WO-8302188 A1 | 6/1983 |
| WO | WO-99/08762 | 2/1999 |
| WO | WO-00/23161 | 4/2000 |
| WO | WO-00/54237 | 9/2000 |
| WO | WO-01/55922 | 8/2001 |
| WO | WO-0173687 A2 | 10/2001 |
| WO | WO-02/47013 | 6/2002 |
| WO | WO-02/082365 | 10/2002 |
| WO | WO-2005/067836 A1 | 7/2005 |

OTHER PUBLICATIONS

Braathen, Anders, et al., "Mobile Music Shopper", http://www.sims.berkeley.edu/~jleon/me221/prelimbizplan.htm, Univeristy of California, Berkeley ME-221 High Tech Product Design and Rapid Manufacturing Final Project,(2002).

Foley, Mary J., "Is 'Autoblogging' the Next Big Thing?", http://www.microsoft-watch.com/article2/0,4248,1095371,00.asp, From the May 6, 2003 issue of Microsoft Watch,(May 2003).

Takabayashi, Satoru, "PlayStand: "Put and Play" CD Player". http://www.namazu.org/~satoru/playstand/index.html, (Aug. 2002).

* cited by examiner

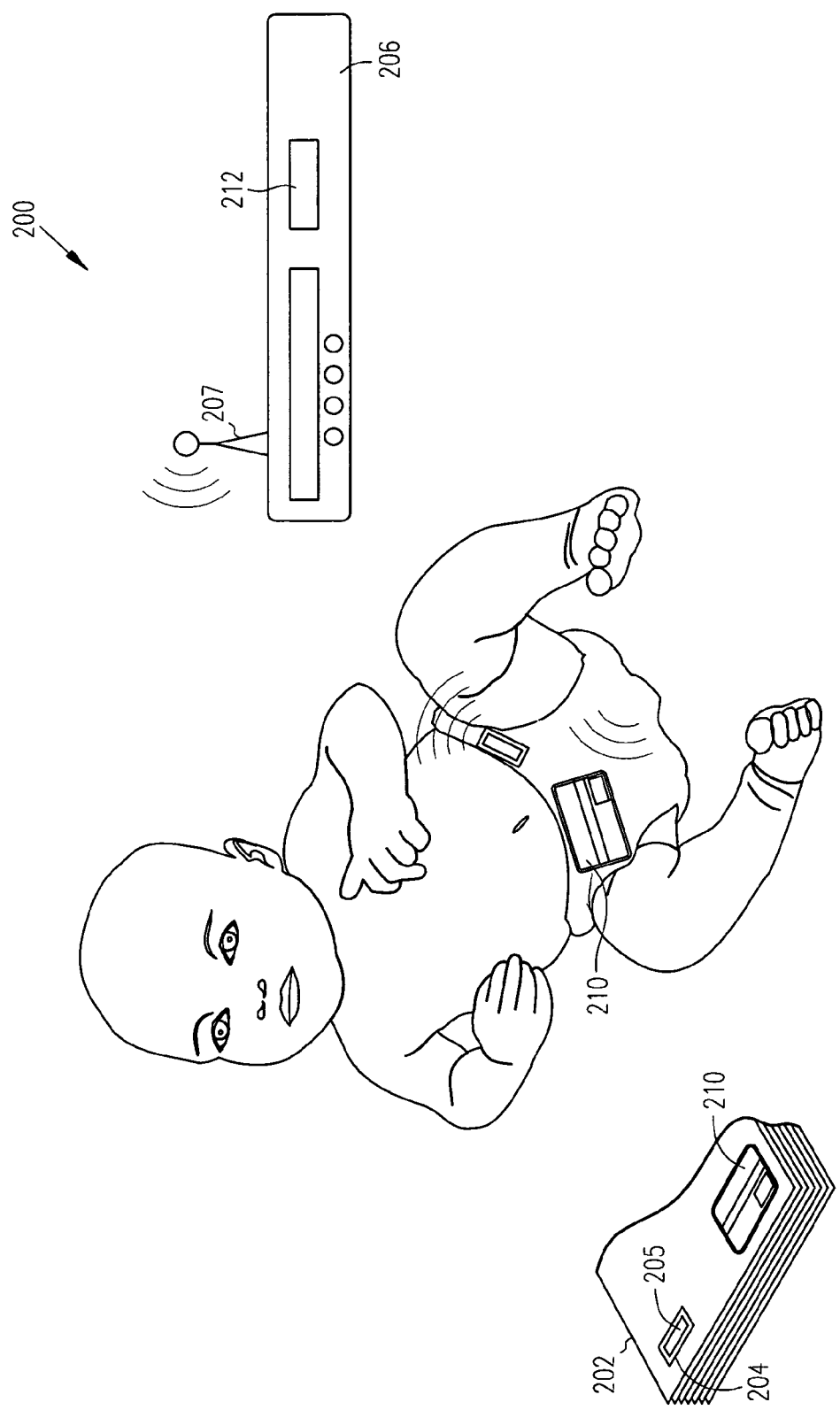

SYSTEM AND METHOD FOR IDENTIFYING DISPOSABLE ABSORBENT PRODUCTS

FIELD OF THE INVENTION

This invention relates to systems and methods for identifying disposable absorbent products, and in particular to systems and methods that play media based on the identity of the disposable absorbent products.

BACKGROUND OF THE INVENTION

Using imagination is important to a child's development. One example is where a child interacts with toys as part of imaginary play.

Computer technology has brought about the development of interactive toys and games. When a toy includes interactive features, the degree of enjoyment and/or educational stimulation that a child can get from the toy is typically enhanced.

Some interactive toys and games may include embedded electronic sensors that can detect one or more actions taken by the child. The interactive toys may further include a control device that generates a particular operation in response to the child's actions. There are also toys that include a speaker which is coupled to the control device. The control device typically causes the speaker to emit audible signals in response to external stimulation, or communication, provided by the child or other toys. The control device typically selects the type of audible signal that is emitted by the speaker based on the identity of the external stimulation.

The exchange of information between devices is a broad field that includes many different applications. One common method of exchanging information includes providing machine readable information in barcode form on one item, and then scanning the barcode on the item with scanning equipment. Bar codes are often located on products/packaging to identify products during inventory, distribution and/or automated check out.

Another method of exchanging information includes transmitting and receiving information via "radio" signals. As an example, one or more devices may include passive radiofrequency identification circuits (RFID's), or passive reflector transceivers (PFTs), that are read by another device (e.g., a scanner). In some systems, the scanner activates the RFID, or PFT, via a transmitted signal that has sufficient energy to (i) energize the circuit; and (ii) transmit information from the circuit to the scanner. Some RFID's are capable of sending and receiving information (see, e.g., U.S. Pat. No. 5,030,807, which is incorporated herein by reference).

There are some systems that exchange information relating to products which are available for purchase. U.S. Pat. No. 6,084,528 discloses a wireless scanning device that includes a video or audio display. The scanning device provides information relating to a particular product that is associated with the scanned symbol.

One drawback with such a system is that the scanning device is typically not readily moved due to its size and weight. Another drawback is that the scanning device typically only includes information relating to the product that is scanned.

There are some known scanning devices that are small enough to be carried at all times. Some examples of scanning devices include pens, wands, keys, key fobs, pagers, flashlights and handheld computers.

One example of a handheld portable scanning device is described in WO 01/73687. During operation the scanning device initially receives information by scanning information on a product. The scanner then stores the information within the scanning device. The scanning device is then transported to a computer or internet portal where the information is downloaded to provide access to databases that contain information about the originally scanned objects. WO 01/73687 also describes storing information related to a consumer's preferences.

SUMMARY OF THE INVENTION

The present invention relates to a system that includes a plurality of disposable absorbent products where at least one of the disposable absorbent products includes a tag. The system further includes a reader that identifies the tags on the plurality of disposable absorbent products and plays media based on the identity of the tags.

In some sample forms of the system, each of the tags (e.g., barcodes) on the plurality of disposable absorbent products is different from the other tags such that the reader plays different media based on the identity of the tags. As examples, the plurality of disposable articles may be diapers, pull-ups, adult incontinence devices or wipes. In addition, the reader may be included in a toy or diaper changing pad (among other items) that plays media such as audio and/or video recordings.

In some forms, the media that is played by the reader may include educational materials, customized information as to a user of the plurality of absorbent products, and/or product-related information. It should be noted that the product-related information may include information related to contests and/or promotions involving the plurality of absorbent products or another type of product. In addition, depending on the application where the system is used, the tags and/or reader may include customized information related to a user of the plurality of disposable absorbent products.

In some forms of the system, the plurality of disposable absorbent products may be a first plurality of disposable absorbent products such that the system further includes a second plurality of disposable absorbent products. The second plurality of disposable products may include tags that are different than the tags on the first plurality of disposable absorbent products. In some forms, the reader may play one type of media when a tag identifies a product in the first plurality of disposable absorbent products and play different media when a tag identifies a product in the second plurality of disposable absorbent products.

It should be noted that the reader may be a first reader such that the system further includes a second reader that plays media based on the identity of the tags. In some forms, the first reader plays different media than the second reader.

There may be some sample forms of the system where each of the tags includes a transmitter, and the reader includes a receiver that identifies the transmitters. In some forms, the system may include multiple readers that monitor a location of the tags. In other forms, the reader may monitor a condition (e.g., wetness) of the tags such that the reader plays media depending on the condition of the tags.

In another aspect, the present invention relates to a system that includes a plurality of disposable absorbent products where at least one of the disposable absorbent products includes a tag. The system further includes a reader that identifies the tags on the plurality of disposable absorbent products and provides information relating to one other product based on the identity of the tags.

In some forms, the plurality of disposable absorbent products may be diapers or pull-ups, and the one other product may be food or toys (among other products or services). In addition, the reader may play media that includes information (e.g., promotional information) relating to the other product based on the identity of the tags.

In yet another aspect, the present invention relates to a system that includes a plurality of disposable absorbent products where at least one of the disposable absorbent products includes a tag. The system further includes a reader that identifies the tags on the plurality of disposable absorbent products and a card that is attached to at least one of a plurality of disposable absorbent products. The reader sends a signal to the card to play media (e.g., audio recordings) based on the identity of the tags. In some forms, the card may be flexible to facilitate attachment of the card to at least one of the plurality of disposable absorbent products.

In still another aspect, the present invention relates to a method that includes marking a plurality of disposable absorbent products (e.g., diapers) with one or more tags, and providing a reader that plays media based on the identity of the tags. It should be noted that marking a plurality of disposable absorbent products with a tag may include marking each, or some, of the plurality of disposable absorbent products with a tag. In addition, each of the tags may be the same, partially the same, or unique, depending on the application where the system is used.

In some forms, marking a plurality of disposable absorbent products with a tag includes (i) marking the plurality of disposable absorbent products with a barcode; or (ii) placing a transmitter on the plurality of disposable absorbent products. When a transmitter is placed on the plurality of disposable absorbent products, providing a reader may include providing a receiver (e.g., an RFID scanner) that identifies the transmitters on the plurality of disposable absorbent products.

It should be noted that providing a reader may include providing a reader that monitors a location and/or a condition of the tags on the plurality of disposable absorbent products. As an example, one or more readers may monitor the wetness of the tags on diapers, and then play media that includes an alarm depending on whether the tag is wet.

In some forms, providing a reader that plays media based on the identity of the tags may include providing a reader that plays different media based on the identity of the tags. In addition, providing a reader that plays media may include providing a reader that (i) plays audio and/or video recordings; (ii) emits an aroma; (iii) plays media with information customized to a user of the plurality of disposable absorbent products; (iv) plays media with educational material; and (v) plays media with product-related information. In addition, the reader may be a first reader such that the method further includes providing a second reader that plays different media than the first reader based on the identity of the tags.

The method may further include selling the plurality of disposable absorbent products (e.g., diapers) to consumers such that providing a reader includes providing a reader to the consumers of the plurality of disposable absorbent products. In addition, providing a reader to the consumers of the plurality of disposable absorbent products may include (i) selling the reader to the consumers; and/or (ii) providing media to the consumers (e.g., on a CD or over the internet) that can be played by the reader.

In still another aspect, the present invention relates to a method that includes marking at least one of a plurality of disposable absorbent products (e.g., diapers) with a tag. The method further includes providing a reader to consumers that supplies information to consumers relating to another product based on the identity of the tags. It should be noted that supplying information to consumers relating to another product may include supplying information relating to toys or food (among other products or services).

In some forms of the method, providing a reader to consumers may include providing a reader that plays media with information (e.g., promotional information) relating to another product based on the identity of the tags. In addition, providing a reader to consumers may include providing a reader to a seller of another product so that consumers can access the reader at the other seller's place of business.

The purposes and features of the present invention will be set forth in the description that follows. Additional features of the invention will be realized and attained by the product and processes particularly pointed out in the written description and claims hereof, as well as from the appended drawings.

It is to be understood that both the foregoing general description and the following detailed description are exemplary and are intended to provide further explanation of the invention claimed. The accompanying drawings, which are incorporated in and constitute part of this specification, are included to illustrate and provide a further understanding of the invention.

BRIEF DESCRIPTION OF THE DRAWINGS

The present invention will be more fully understood, and further features will become apparent, when reference is made to the following detailed description and the accompanying drawings. The drawings are merely representative and are not intended to limit the scope of the claims. Like parts depicted in the drawings are referred to by the same reference numerals.

FIGS. 1-11 illustrate various systems and methods for performing the present invention.

DETAILED DESCRIPTION

In the following detailed description, reference is made to the accompanying drawings, which show specific embodiments in which the invention may be practiced. These embodiments are described in sufficient detail to enable those skilled in the art to practice the invention. It is to be understood that other embodiments may be utilized and structural changes made, such that the following detailed description is not to be taken in a limiting sense.

Figure 1:
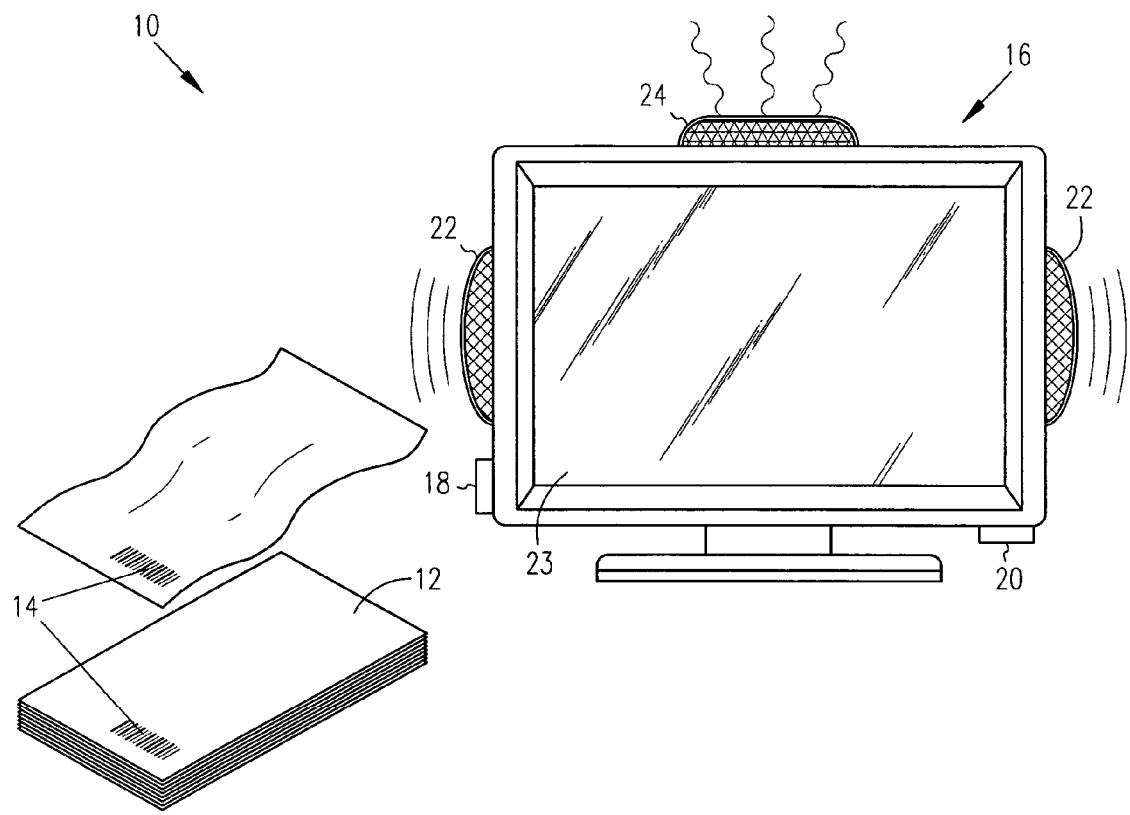

FIG. 1 shows a system 10 that includes a plurality of disposable absorbent products 12. As used herein, "plurality of disposable absorbent products" includes a plurality of diapers, pull-ups, adult incontinence devices, wipes and the like (e.g., wipes 12 are shown in FIG. 1). At least one of the disposable absorbent products 12 includes a tag 14. The system 10 further includes a reader 16 that identifies the tags 14 on the plurality of disposable absorbent products 12 and plays media 20 based on the identity of the tags 14. In some forms, each of the tags 14 on the plurality of disposable absorbent products 12 is different from the other tags 14 such that the reader 16 plays different media 20 based on the identity of each tag 14. In the example embodiment illustrated in FIG. 1, the tags 14 are barcodes 14 and the reader 16 includes a scanner 18 that identifies the barcodes 14.

It should be noted that the media 20 may be stored in the reader 16, or a device that is operatively coupled to reader 16. In some forms, the media 20 may include audio recordings that are played through speakers 22 on the reader 16 and/or video recordings that are played through a monitor 23 on the reader 16. The media 20 may also include an aroma that is distributed through a dispersion system 24 on the reader 16. The media 20 may be played by the reader 16 at random or in a pre-selected pattern.

The type of information included in the media 20 will vary depending on the application where the system is used. As an example, the media 20 may include educational materials and/or product-related information. In some forms, the product-related information may include information involving contests or promotions related to the plurality of disposable products 12.

The media 20 may also include customized information related to a user of the plurality of disposable products 12. As an example, if the reader 16 plays an audio-visual story when a barcode 14 is scanned by scanner 18, the story may be modified to include a particular child's name that is associated with the barcode 14 that was scanned. It should be noted that the customized information may be stored within the information associated with the tag 14, or stored in the reader 16. The reader 16 is then able to associate the customized information with one or more tags 14. In some forms, the reader 16 allows a user of the plurality of disposable products 12 to input customized information into the reader 16. The customized information may then be incorporated into the media 20.

In addition, when the plurality of disposable products 12 is diapers, the media 20 played by the reader 16 may create an interactive environment with a child. In some forms, parents could buy or download media 20 (e.g., from the Internet) that may be played by one or more readers 18 to support an interactive environment. The interactive environment may be theme-based such that the media references certain types of stories and fictional characters (e.g., Barney, Cinderella and Sesame Street). The receiver 16 may also allow parents, or others, to record voices (e.g., using a digital voice recorder) and/or customize the names that are used in theme-based stories.

Figure 2:
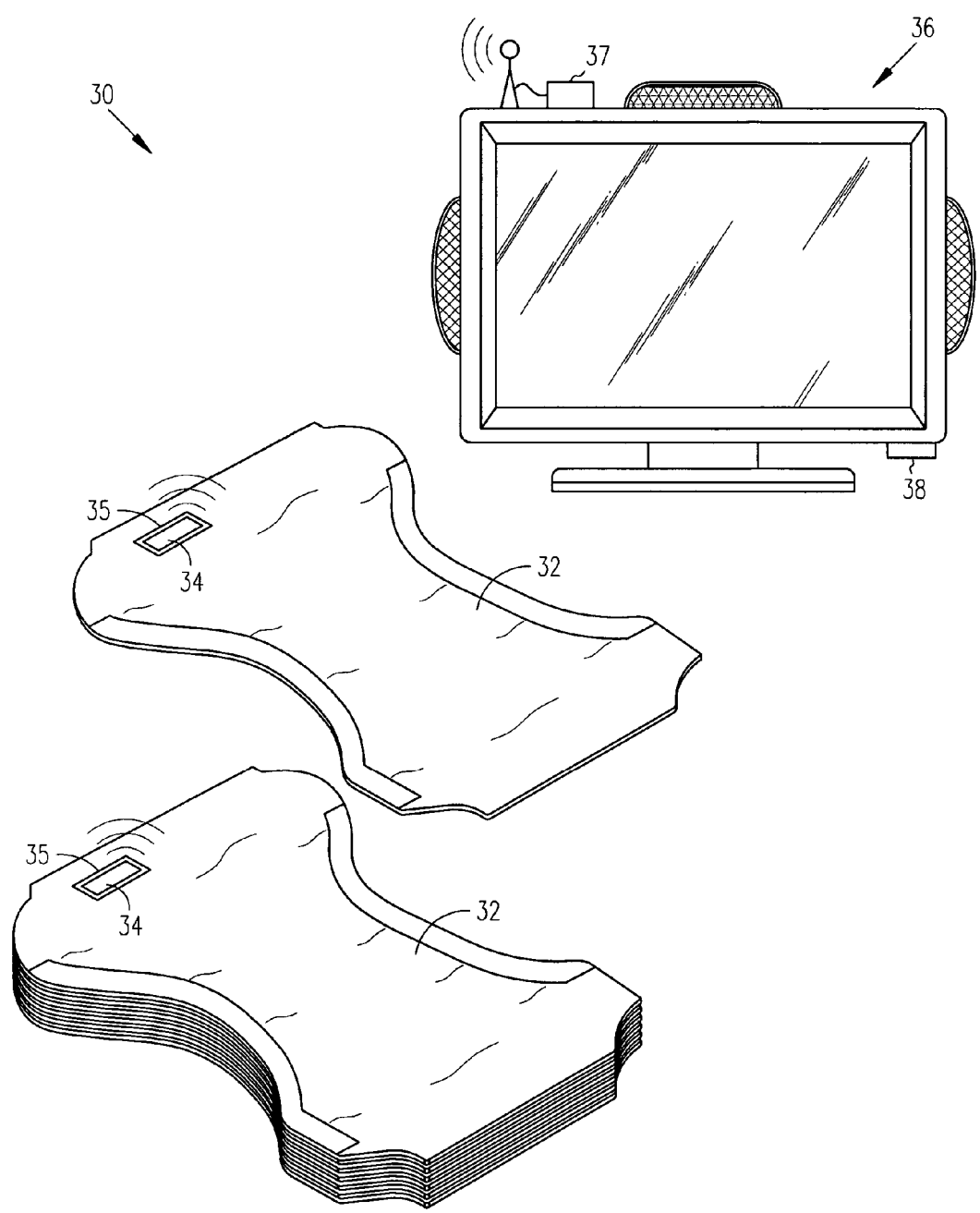

FIG. 2 illustrates another example system 30 that includes a plurality of disposable absorbent products 32 (e.g., diapers 32 are shown in FIG. 2). At least one of the disposable absorbent products 32 includes a tag 34. The system 30 further includes a reader 36 that is similar to reader 16. The reader 36 identifies the tags 34 on the plurality of disposable absorbent products 32 and plays media 38 based on the identity of the tags 34.

In the example form illustrated in FIG. 2, each of tags 34 includes a transmitter 35 that sends information (e.g., via a radio frequency) to a receiver 37 which is operatively coupled to the reader 36. The receiver 37 identifies the tags 34 based on information received from the transmitters 35.

In some forms, the reader 36 may be used to monitor the presence of one or more tags 34 on the plurality of disposable products 32. As an example, the reader 36 may play media 38 that indicates a child wearing the diaper 32 is in the vicinity of the reader 36, or has left the vicinity of the reader 36.

It should be noted that the tags 34 and reader 36 may use radiofrequency identification (RFID). RFID is the use of radio frequency signals to read information on a small tag. RFID tags can be passive tags that rely on RF energy from an RFID scanner to activate a circuit and provide power to a small antenna that retransmits a weak signal, or they can be active tags that have their own power source for generating an RF signal containing information to be read by a scanner. Most RFID tags in use contain microchips to provide identity information or other information, but chipless tags and taggants, such as nanobarcodes are also available. It should be noted that the RFID scanners and RFID tags may include any combination of active and passive circuits.

In some forms, the tags are RFID read/write tags (i.e., the tags can supply information and receive information). As an example, one or more of the tags 34 may be supplied with information such as sound bites recorded by parents, caregivers, relatives and teachers (among others). The information is provided to the receiver 37 such that the reader 36 incorporates the information into the media 38 that is played by the reader 36.

Figure 3:
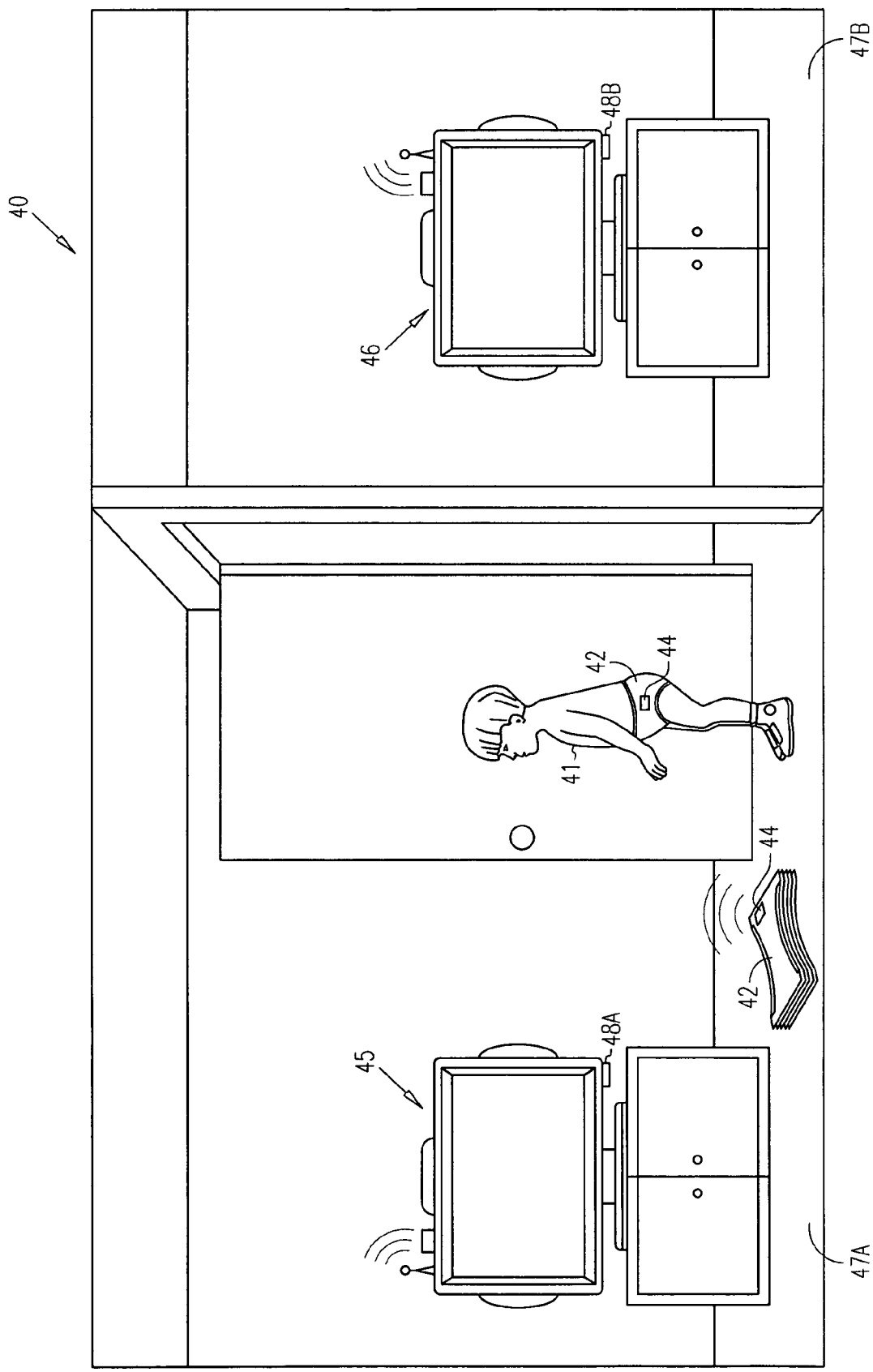
Figure 4:
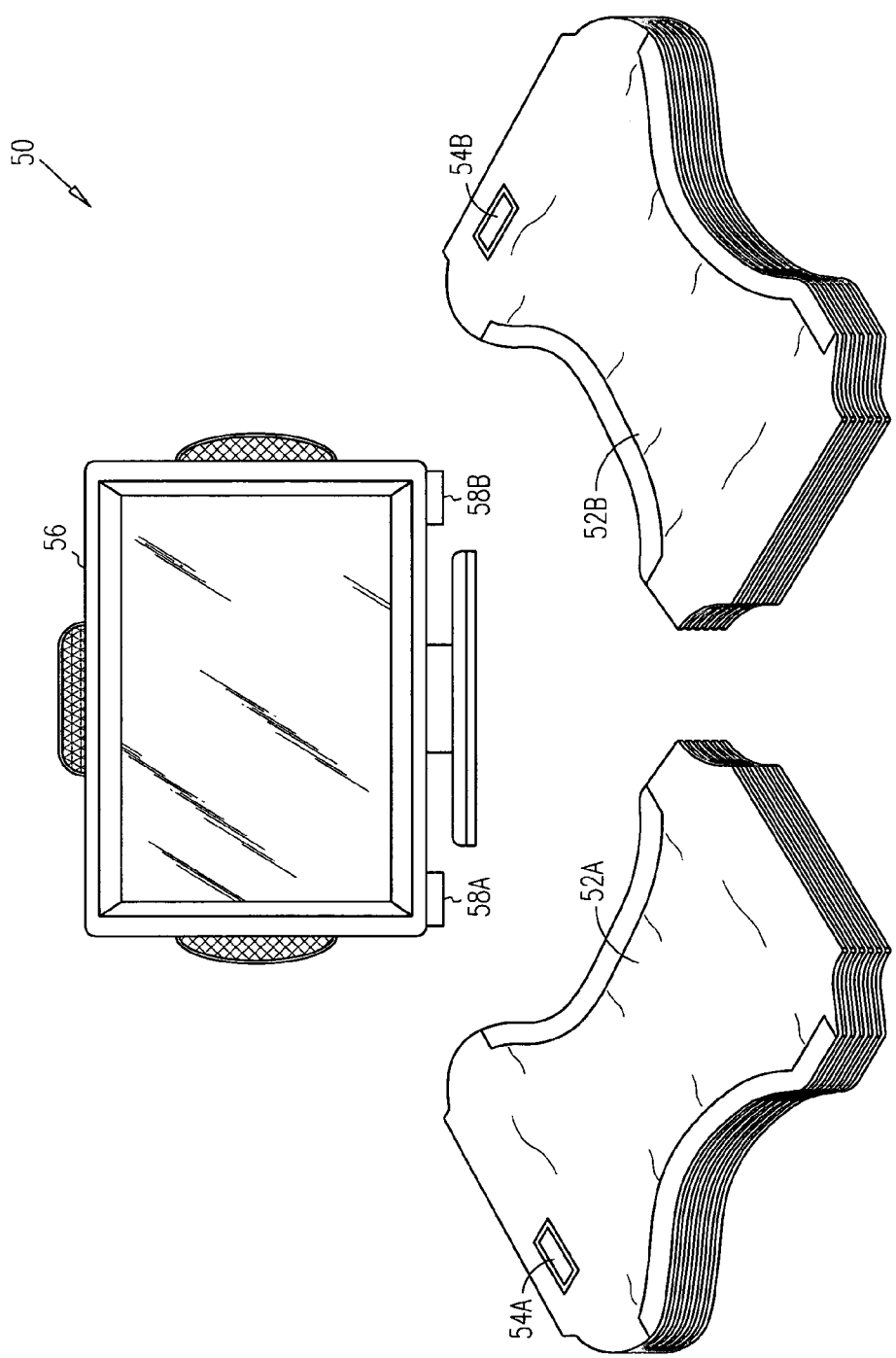

FIG. 3 shows another example system 40 that includes a plurality of disposable absorbent products 42 (e.g., diapers 42 are shown in FIG. 4). At least one of the disposable absorbent products 42 includes a tag 44 (see, e.g., the diaper 42 worn by the toddler 41). The system 40 further includes a first reader 45 and a second reader 46. The first and second readers 45, 46 identify the tags 44 on the diapers 42.

In some forms, the first and second readers 45, 46 may be used to monitor the presence of a tag 44 on the diaper 42 worn by the infant 41. As an example, the first reader 45 may be in a first room 47A. The first reader 45 may play media 48A that indicates the toddler 41 is in the first room 47A. In addition, the second reader 46 may be in a second room 47B. The second reader may play media 48B that indicates the toddler 41 is in the vicinity of the second room 47B.

FIG. 4 shows another example system 50 that includes a first plurality of disposable absorbent products 52A and a second plurality of disposable absorbent products 52B (e.g., diapers 52A, 52B are shown in FIG. 3). At least some of the plurality of disposable absorbent products 52A, 52B includes respective tags 54A, 54B. The system 50 further includes a reader 56 that is similar to one or more readers described previously.

In the example form illustrated in FIG. 4, each of tags 54A on the first plurality of disposable absorbent products 52A is different from the tags 54B on the second plurality of disposable absorbent products 52B. In some forms, the reader 56 plays one type of media 58A when a tag 54A identifies a product in the first plurality of disposable absorbent products 52A and plays different media 58B when a tag 54B identifies a product in the second plurality of disposable absorbent products 52A.

It should be noted that the interaction of two or more tags with a reader may cause the reader to play one or more special types of media. The tags may be from the same group of products or different groups of products depending on the application. As an example, the name of a child and the child's sibling may both be used in a story that is played by a reader.

Figure 5:
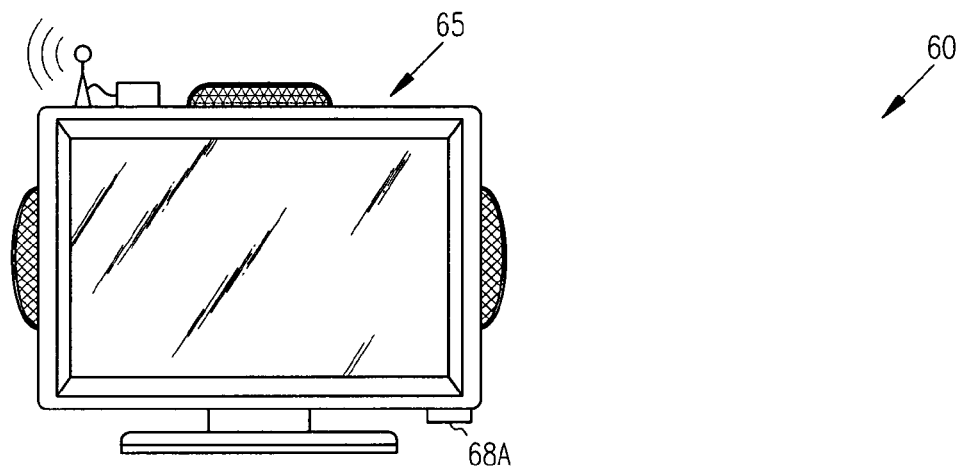
Figure 5:
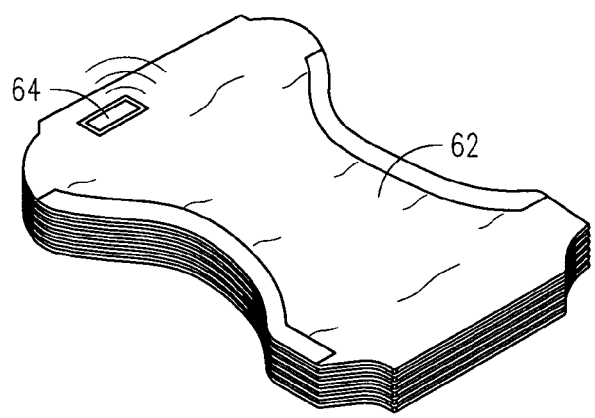
Figure 5:
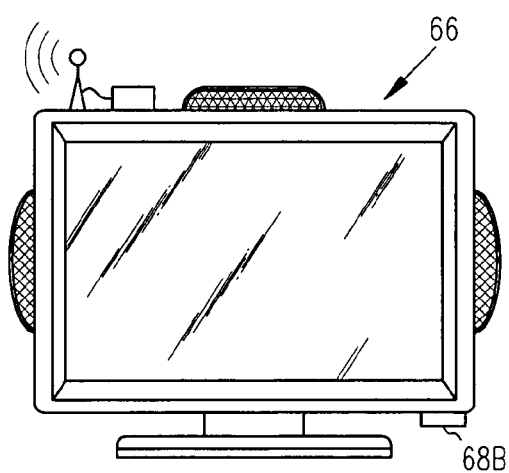

FIG. 5 shows another example system 60 that includes a plurality of disposable absorbent products 62 (e.g., diapers 62 are shown in FIG. 5). In the example form illustrated in FIG. 5, at least one of the disposable absorbent products 62 includes a tag 64. The system 60 further includes a first reader 65 and a second reader 66. The first and second readers 65, 66 may be any type of reader that is described or referenced herein.

The first and second readers 65, 66 identify the tags 64 on the plurality of disposable absorbent products 62. In some forms, the first reader 65 may play one type of media 68A based on the identity of the tags 64 when the tags 64 are scanned by the first reader 65. In addition, the second reader 66 may play another type of media 68B based on the identity of the tags 64 when the tags 64 are scanned by the second reader 66.

Figure 6:
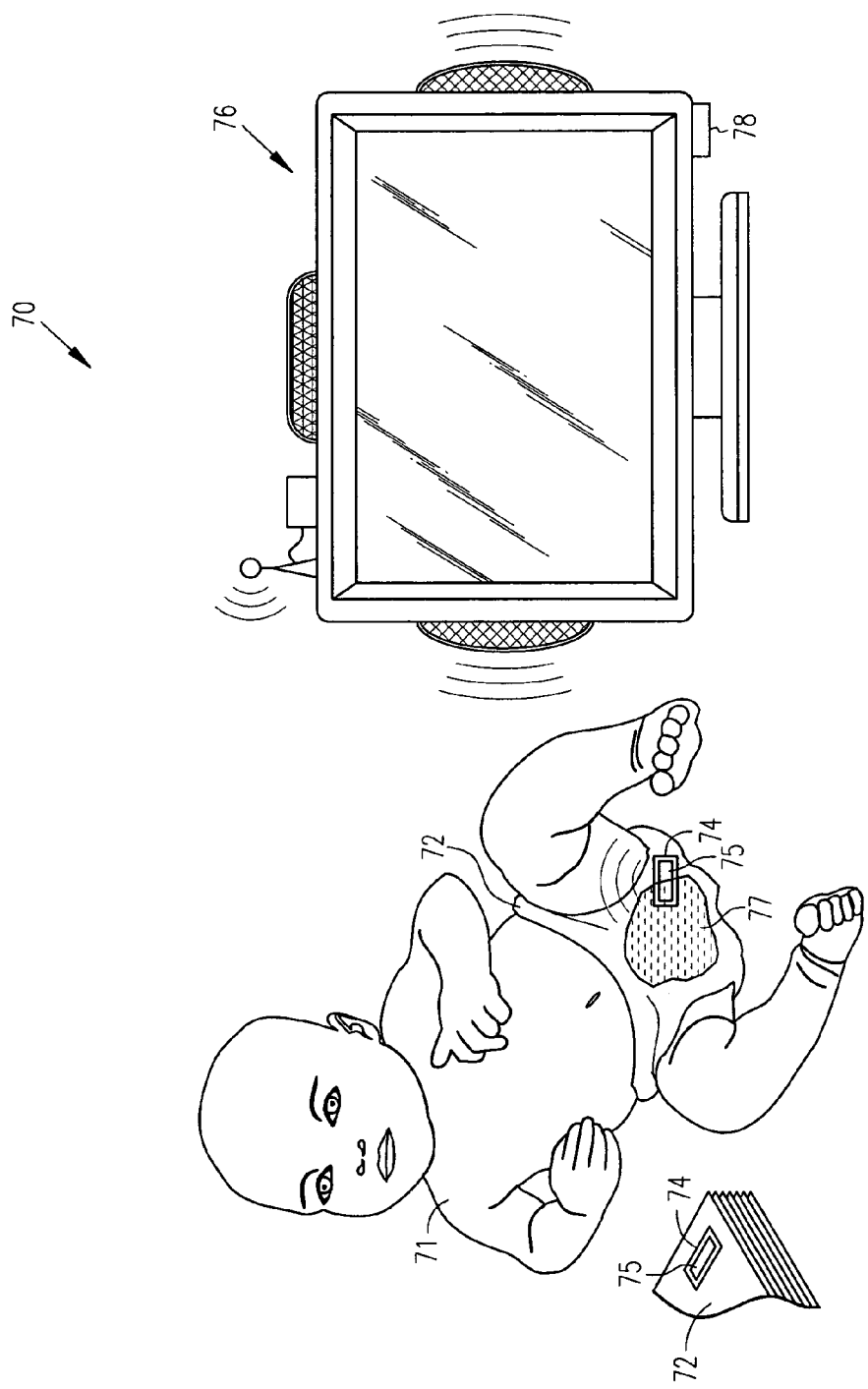

FIG. 6 shows another example system 70 that includes a plurality of disposable absorbent products 72 (e.g., diapers 72 are shown in FIG. 6). At least one of the disposable absorbent products 72 includes a tag 74 (see, e.g., the diaper 72 worn by the infant 71). The system 70 further includes a reader 76 that is similar to one or more of the readers described or referenced herein. The reader 76 monitors a condition of the tags 74 using a sensor 75 that is operatively coupled to the tags 74.

The type of condition that is monitored by the sensors 75 will depend in part on the application where the system 70 is used. Some example conditions that may be monitored by the tags 74 include wetness and temperature (among others).

In the example form illustrated in FIG. 6, the tags 74 include a sensor 75 that monitors when the diaper 72 is holding waste 77. When the diaper 72 is holding waste 77, the tag 74 sends information to the reader 76 which indicates that the diaper 72 contains waste 77. Once the reader 76 receives such information, the reader 76 may play media 78 that indicates the diaper 72 includes waste 77. In some forms, the reader 76 may play one type of media 78 when the diaper 72 is dry and play another type of media 78 when the diaper 72 is wet. In addition, the media 78 may include information that is meant to promote worthwhile behavior, such as to provide potty training.

Figure 7:
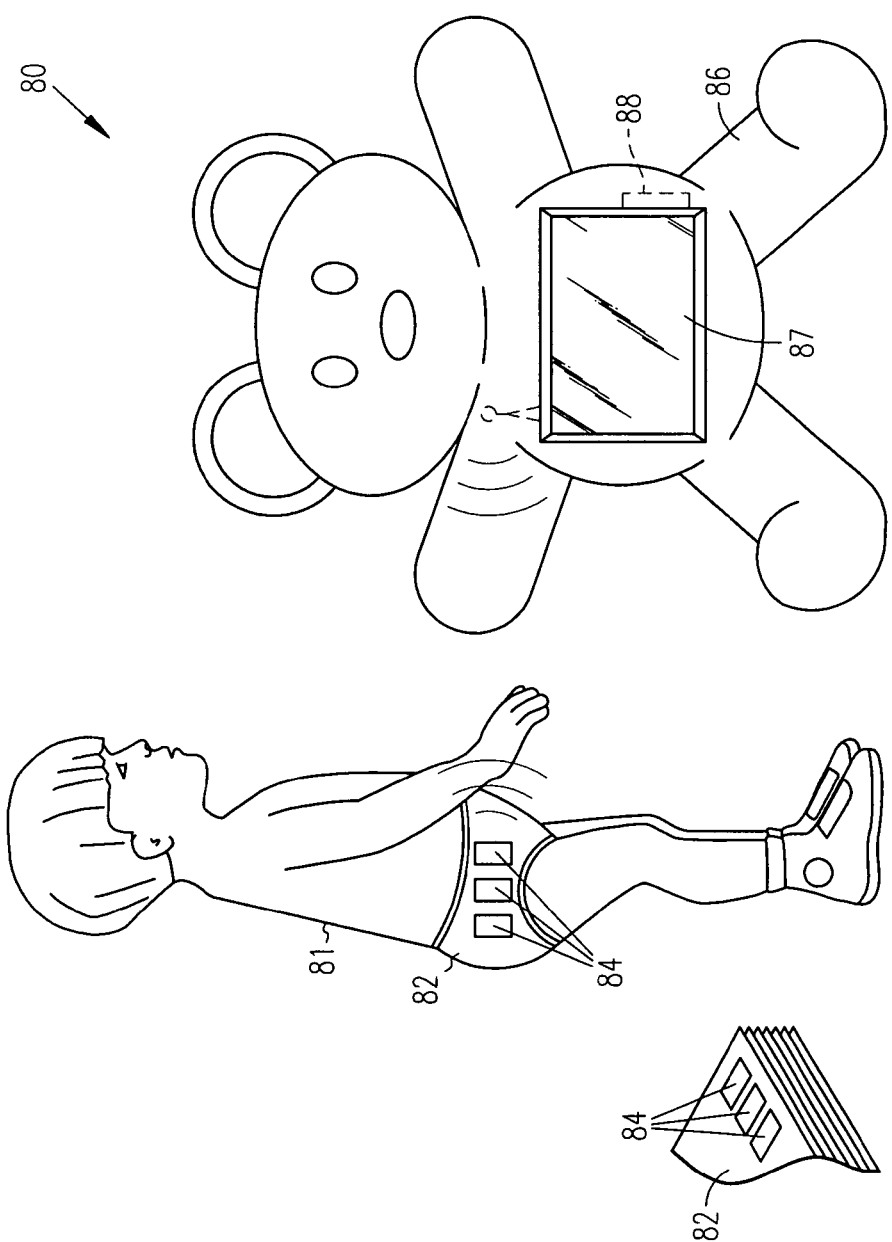

Although FIGS. 1-6 illustrate similar readers, it should be noted that the reader may be incorporated into different types of devices. FIG. 7 shows another example system 80 that includes a plurality of disposable absorbent products 82 (e.g., diapers 82 are shown in FIG. 7). At least one of the disposable absorbent products 82 includes one or more tags 84 (see, e.g., the diaper 82 being worn by the infant or toddler 81).

The system 80 further includes a reader 86 that is in the form of a stuffed toy 86. The toy reader 86 identifies the tags 84 and plays media 88 based on the identity of the tags 84. It should be noted that any type of toy may be used in the system 80.

Using a toy to play the media 88 enhances the stimulation enjoyed by the infant 81. The enhanced stimulation may aid in keeping the infant 81 occupied during certain activities (e.g., changing a diaper 82). In the example toy reader 86 illustrated in FIG. 7, the toy reader 86 includes a monitor 87 that plays video media 88. In some forms of the system 80, the toy reader 86 may play more than one type of media 88.

Figure 8:
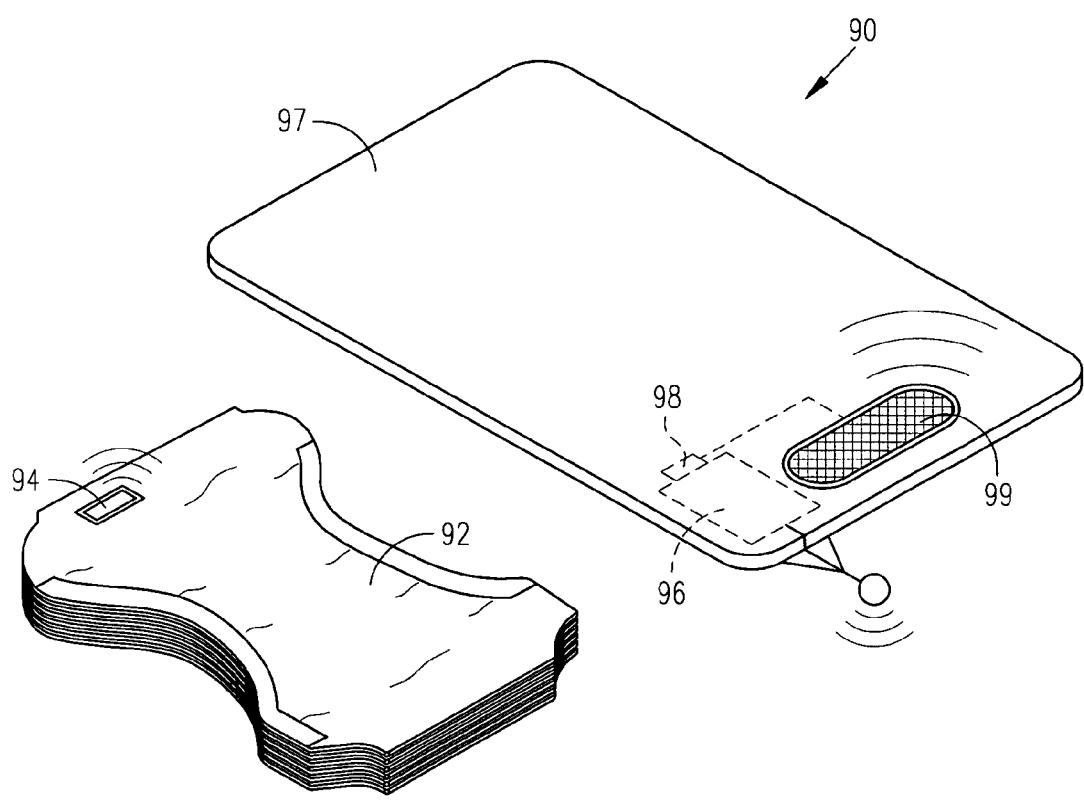

FIG. 8 shows another example system 90 that includes a plurality of disposable absorbent products 92 (e.g., diapers 92 are shown in FIG. 8). At least one of the disposable absorbent products 92 includes one or more tags 94. The system 90 further includes a reader 96 that is formed into part of a diaper changing pad 97 which plays media 98 based on the identity of the tags 94.

In the example form illustrated in FIG. 8, the diaper changing pad 97 includes a speaker 99 that plays audio media 98. The size and shape of the diaper changing pad 97 and the type of media 98 that is played by the reader 96 will depend on the application where the system 90 is used. It should be noted that in other forms of the system 90, the reader 96 may be operatively associated with a car seat cover, a high chair pad, a play mat, a crib liners and a disposable protective polymeric sheet (among other items).

Figure 9:
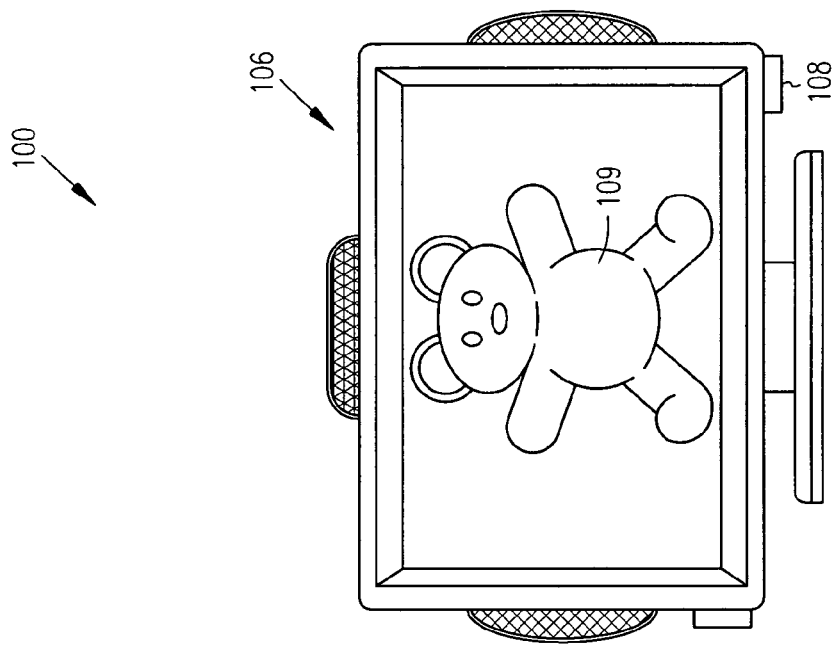
Figure 9:
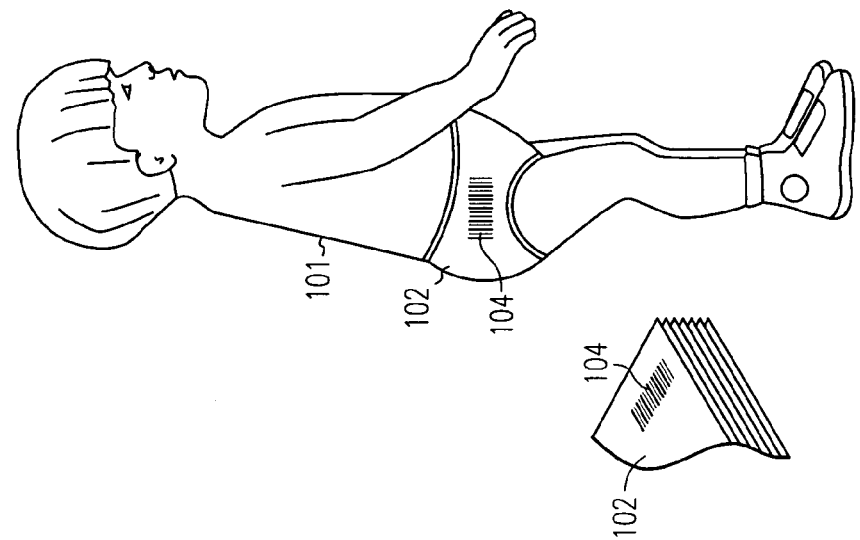

Another example system 100 is illustrated in FIG. 9. The system 100 includes a plurality of disposable absorbent products 102 (e.g., diapers 102 are shown in FIG. 9 with one of diapers 102 being worn by a child 101). In the example system 100 illustrated in FIG. 9, at least one of the diapers 102 includes a tag 104. The system 100 further includes a reader 106 that identifies the tags 104 on the plurality of disposable absorbent products 102. The reader 106 plays media 108 that provides information relating to one other product (or service) based on the identity of the tags 104.

In the example form of the system illustrated in FIG. 9, the one other product is toys (see e.g., toy 109 on reader 106). As an example, the reader 106 may play media 108 that includes information relating to toys based on the identity of the tag 104. The tag 104 may indicate the age, gender and/or name (among other things) of the child 101 wearing the diaper 102. Therefore, the reader 106 is able to select appropriate media to play for the child 101 based on the identity of the tag 104. The information in the media may relate to promotions and/or contests involving toy products.

Figure 10:
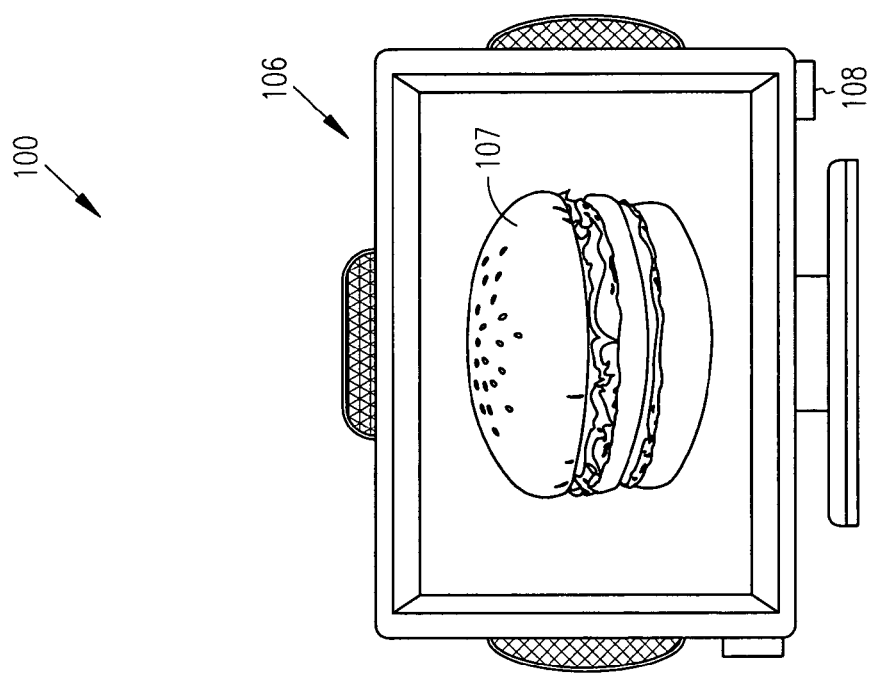
Figure 10:
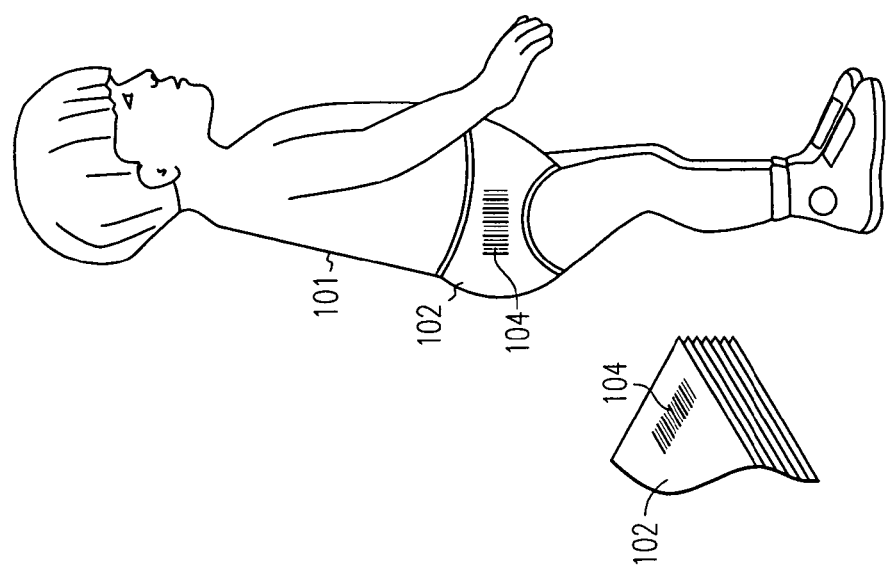

FIG. 10 illustrates another example embodiment of the system 100. In the example embodiment shown in FIG. 10, the one other product is food (see e.g., hamburger 107 on reader 106). As an example, the identity of tag 104 may trigger the reader 106 to play media 108 with information relating food discounts, giveaways or menu choices directed to children.

It should be noted that in example forms illustrated in FIGS. 9 and 10 the reader 106 may be connected to the internet at a retailer of the one other product. In addition, the reader 106 may be able to download media that includes information as to promotions or contests relating to the one other product. In other forms, a consumer may bring media (e.g., on a disk) that can be downloaded to the reader at the retailer's location.

FIG. 11 illustrates another example system 200 that includes a plurality of disposable absorbent products 202 (e.g., diapers 202 are shown in FIG. 11). At least one of the disposable absorbent products 202 includes a tag 204. The system 200 further includes a reader 206 that identifies the tags 204 on the plurality of disposable absorbent products 202.

In the example form illustrated in FIG. 11, each of tags 204 includes a transmitter 205 that sends information (e.g., via a radio frequency) to a receiver 207 which is operatively coupled to the reader 206. The receiver 207 identifies the tags 204 based on information received from the transmitters 205.

The system 200 further includes one or more cards 210 that are attached to at least one of the plurality of disposable absorbent products 202. The cards 210 may be attached to one, some or all of the plurality of disposable absorbent products 202. In some forms, more than one card 210 may be attached to one or more of the plurality of disposable absorbent products 202.

Based on the identity of the tags 204, the reader 206 sends signals (e.g., wireless RF signals) to the cards 210 that instruct the cards 210 to play media 212. It should be noted that the media 212 may be stored in the reader 206 and/or the cards 210. In some forms, the media 212 may include audio recordings that are played by the card 210.

The reader 206 may be capable of being connected to the internet so that parents could download the media 212. In addition, the reader 206 in the system 200 may allow parents, or others, to (i) record voices that may be included in the media 212; and/or (ii) add customized information (e.g., a child's name) that may be included in the media 212.

The type of cards 210 that are used in the system 200 will depend on the application where the cards 210 are used. In some forms, the cards 210 may be flexible to conform to the plurality of disposable absorbent products 202 (e.g., diapers).

It should be noted that the number, size, style and arrangement of the tags in any of the systems described herein will depend on the application where the tags are used, and will be especially dependent on the type of disposable absorbent products where the tags are placed. In addition, the number and different types of media that may be played by the readers in the systems described herein will depend on the application where the systems are used. As used herein, media includes any type of file or storage means (e.g., electronic, magnetic) now known, or developed in the future, that can be played by hardware (e.g., speakers, monitors and/or dispersion systems) either directly or indirectly (i.e., through other hardware and/or software).

Some example methods of the present invention will now be described with reference to FIGS. 1-11. In some forms, the method includes marking at least one of a plurality of disposable absorbent products 12 with a tag 14 and providing a reader 16 that plays media 20 based on the identity of the tags 14 (see, e.g., FIG. 1).

It should be noted marking at least one of a plurality of disposable absorbent products 12 with a tag 14 may include marking some of the plurality of disposable absorbent products 12 with a tag 14 or marking each of the plurality of disposable absorbent products 12 with a unique tag 14. As an example, FIG. 1 illustrates marking a plurality of disposable absorbent products 12 with a barcode 14.

In some forms, the reader 16 may have the ability to download media 20 from the internet based on the identity of the tag 14. The tag 14 may also include information that instructs the reader 16 what media 20 to play from the internet. It should be noted that when the reader is adapted to obtain media from other sources (e.g., the internet), the reader does not necessarily have to store media for different sizes and types of disposable absorbent products 12. The reader 16 may also be able to read CD's (or other electronic media) such that the reader can play multiple types of media 20 based in the identity of the tags 14.

In another form of the method shown in FIG. 2, marking a plurality of disposable absorbent products 32 with a tag 34 includes marking diapers 32 with a tag 34. In other forms, marking a plurality of disposable absorbent products 32 with a tag 34 may include marking pull-ups or adult incontinence articles with a tag 34. In addition, providing a reader may include providing a toy reader (see, e.g., toy reader 86 in FIG. 7).

FIG. 2 also shows that marking at least one of a plurality of disposable absorbent products 32 with a tag 34 may include placing a transmitter 35 on the plurality of disposable absorbent products 32. In addition, providing a reader 36 may include providing a receiver 37 that identifies the transmitters 35 on the plurality of disposable absorbent products 32.

Some other example forms of the method may include providing a reader that monitors the tags on a plurality of disposable absorbent products. It should be noted that providing a reader may include providing a reader 45 that plays media 48A and monitors a location of the tags 44 on the diapers 42 (see, e.g., reader 45 in FIG. 3).

In some forms, the reader 45 is a first reader 45 such that the method further includes providing a second reader 46 that plays media 48B and monitors a location of the tags 44. FIG. 3 shows how the first reader 45 can be used to monitor when an infant 41 is in one room 47A and the second reader 46 can be used to monitor when an infant 41 is in another room 47B.

FIG. 6 illustrates an example form of the method where providing a reader 76 that monitors the tags 74 on the plurality of disposable absorbent products 72 includes providing a reader 76 that monitors a condition of the tags 74. As an example, a reader 76 may be provided that receives signals from a sensor 75 on the tags 74 to monitor chemistry, wetness and/or the temperature of the tags 74. In some forms, the chemistry, wetness and/or temperature of a tag 74 may be used to determine whether there is waste 77 within a diaper 72 that is worn by the infant 71.

Referring again to FIG. 1, it should be noted that providing a reader 16 which plays media 20 based on the identity of the tags 14 may include providing a reader 16 that (i) plays different media 20 based on the identity of the tags 14; (ii) plays audio-video recordings (e.g., on monitor 23 and speaker 22); (iii) emits an aroma (e.g., through dispersion system 24); (iv) plays media 20 with information customized to a user of the plurality of disposable absorbent products 12; and/or (iv) plays media with educational material and/or product-related information.

The method may further include selling the plurality of disposable absorbent products to consumers (see, e.g., wipes 12 in FIG. 1 and diapers 32 in FIG. 2). In addition, providing a reader 16 that plays media may include providing a reader 16 to the consumers of the plurality of disposable absorbent products 12 (e.g., by selling or giving away the reader 16 to the consumers). In some forms, providing a reader 16 to the consumers of the plurality of disposable absorbent products 12 may include providing one or more different types of media 20 to the consumers that can be played by the reader 16. As examples, consumers may be provided with media that is contained on CD's, or directed to one or more websites where the consumer can download media.

FIG. 5 shows that the reader may a first reader 65 such that providing a reader may include providing a first reader 65 that plays one type of media 68A based on the identity of the tags 64. The method may further include providing a second reader 66 that plays different media 68B based on the identity of the tags 64.

FIGS. 9-10 illustrate another example method that includes marking at least one of a plurality of disposable absorbent products (e.g., diapers 102) with a tag 104. The method further includes providing a reader 106 to consumers that supplies information to consumers relating to one other product based on the identity of the tags 104. Some examples include providing a reader 106 that supplies information relating to toys 109 (FIG. 9) and/or food 107 (FIG. 10) (among other products or services).

It should be noted that providing a reader 106 to consumers may include providing a reader 106 that plays media 108 with information (e.g., promotional information) relating to the one other product based on the identity of the tags. In some forms, providing a reader 106 to consumers may include providing a reader 106 to a seller of the one other product.

Providing a reader 106 to a seller of the one other product (e.g., food 107, toys 109) would allow consumers to readily obtain the one other product soon after the reader 106 scans the tags 104 on the plurality of disposable absorbent products 102. In some forms, providing a reader 106 to a seller of the one other product may include providing media 108 with information as to where to locate the one other product within the seller's store. It should be noted that in some forms, the one other "product" may be a service that is performed (e.g., dry-cleaning or making travel arrangements).

The type of disposable absorbent article, tag and reader that are used in the described methods depends on the application where the disposable absorbent products, tags and readers are used. In addition, the type of media, including the type of information supplied by the media, will depend on the application where the system is used.

The operations discussed above with respect to the described methods may be performed in a different order from those described herein. In addition, FIGS. 1-11 are representational and are not necessarily drawn to scale. Certain proportions thereof may be exaggerated, while others may be minimized.

While the invention has been described in detail with respect to the specific aspects thereof, it will be appreciated that those skilled in the art, upon attaining an understanding of the foregoing, may readily conceive of alterations to, variations of, and equivalents to these aspects which fall within the spirit and scope of the present invention, which should be assessed accordingly to that of the appended claims.

We claim:

1. A system comprising:
   a plurality of disposable absorbent products, wherein at least one of said disposable absorbent products includes a tag, each of said tags including a transmitter; and
   a reader that includes a receiver which identifies said transmitters and plays media based on the identity of said tags.

2. The system of claim 1 wherein said reader monitors a location of said tags.

3. The system of claim 1 wherein each tag on said plurality of disposable absorbent products is different from other tags on said plurality of disposable absorbent products, and said reader plays different media based on the identity of said tags.

4. The system of claim 1 wherein said plurality of disposable absorbent products is diapers.

5. The system of claim 1 wherein said plurality of disposable absorbent products is wipes.

6. The system of claim 1 wherein said reader is included in a toy.

7. The system of claim 1 wherein said reader is operatively associated with an item selected from the group consisting of a changing pad, a play mat, a car seat, a high chair pad, a protective polymeric sheet and a crib liner.

8. The system of claim 1 wherein said media includes audio recordings.

9. The system of claim 1 wherein said media includes video recordings.

10. The system of claim 1 wherein said media includes aroma emitted by said reader.

11. The system of claim 1 wherein said reader is a first reader and the system further comprises a second reader that plays media based on the identity of the tags, the first reader playing different media than the second reader.

12. A system comprising:
    a first plurality of disposable absorbent products, wherein at least one of said first plurality of disposable absorbent products includes a tag, each of said tags including a transmitter;
    a second plurality of disposable absorbent products, wherein at least one of said second plurality of disposable absorbent products includes a tag, each of said tags including a transmitter; and
    a reader that includes a receiver which identifies said transmitters and plays media based on the identity of said tags, wherein said reader plays one type of media when a tag identifies a product in said first plurality of disposable absorbent products and plays different media when a tag identifies a product in said second plurality of disposable absorbent products.

13. The system of claim 12 wherein said first plurality of disposable absorbent products is diapers and said second plurality of disposable absorbent products is wipes.

14. The system of claim 12 wherein said reader is included in a toy.

15. The system of claim 12 wherein said reader is operatively associated with an item selected from the group consisting of a changing pad, a play mat, a car seat, a high chair pad, a protective polymeric sheet and a crib liner.

16. The system of claim 12 wherein said media includes audio recordings.

17. A system comprising:
    a plurality of disposable absorbent products, wherein at least one of said disposable absorbent products includes a tag; and
    a reader that identifies said tags on said plurality of disposable absorbent products, wherein said reader provides information relating to one other product based on the identity of said tags.

18. The system of claim 17 wherein said plurality of disposable absorbent products is diapers, and said one other product is food.

19. The system of claim 17 wherein said plurality of disposable absorbent products is diapers, and said one other product is toys.

20. The system of claim 17 wherein said reader provides promotional information relating to said one other product based on the identity of said tags.

21. A method comprising:
    marking at least one of a plurality of disposable absorbent products with a tag by placing a transmitter on some of the plurality of disposable absorbent products; and
    providing a reader that includes a receiver which identifies the transmitters on the plurality of disposable absorbent products and plays media based on the identity of the tag.

22. The method of claim 21 wherein marking at least one of a plurality of disposable absorbent products with a tag includes marking some diapers with a tag.

23. The method of claim 21 wherein providing a reader that includes a receiver which identifies the transmitters on the plurality of disposable absorbent products includes providing a reader that monitors a location of the tags.

24. The method of claim 21 wherein providing a reader that plays media based on the identity of the tags includes providing a reader that plays different media based on the identity of the tags.

25. The method of claim 21 wherein providing a reader that plays media includes providing a reader that plays audio-video recordings.

26. The method of claim 21 wherein providing a reader that plays media includes providing a reader that emits an aroma.

27. The method of claim 21 wherein said reader is a first reader, and the method further comprises providing a second reader that plays different media based on the identity of the tags.

28. The method of claim 21 wherein providing a reader includes providing a reader to consumers of the plurality of disposable absorbent products.

29. The method of claim 28 wherein providing a reader to consumers includes providing a toy to consumers.

30. The method of claim 21 further comprising selling the plurality of disposable absorbent products to consumers.

31. The method of claim 21 wherein providing a reader to the consumers of the plurality of disposable absorbent products includes selling the reader to the consumers.

32. The method of claim 21 wherein providing a reader to the consumers of the plurality of disposable absorbent products includes providing media to the consumers that can be played by the reader.

33. The method of claim 32 wherein providing media to the consumers that can be played by the reader includes providing media to the consumers over the internet.

34. A method comprising:
marking at least one of a plurality of disposable absorbent products with a tag; and
providing a reader to consumers of the plurality of disposable absorbent products such that the reader supplies information to the consumers relating to one other product based on the identity of the tags.

35. The method of claim 34 wherein marking at least one of a plurality of disposable absorbent products with a tag includes marking diapers with a tag.

36. The method of claim 34 wherein supplying information to consumers relating to one other product includes supplying information relating to a toy product.

37. The method of claim 34 wherein supplying information to consumers relating to one other product includes supplying information relating to a food product.

38. The method of claim 34 wherein providing a reader to consumers includes providing a reader that plays media with information relating to the one other product based on the identity of the tags.

* * * * *